United States Patent [19]
Camden

[11] Patent Number: 5,929,099
[45] Date of Patent: Jul. 27, 1999

[54] PHARMACEUTICAL COMPOSITION FOR INHIBITING THE GROWTH OF CANCERS

[75] Inventor: James Berger Camden, West Chester, Ohio

[73] Assignee: Procter & Gamble Co., Cincinnati, Ohio

[21] Appl. No.: 08/680,470

[22] Filed: Jul. 15, 1996

[51] Int. Cl.$^6$ .................................................. A61K 31/425
[52] U.S. Cl. .......................... 514/365; 514/372; 514/388; 514/394; 514/449
[58] Field of Search ..................................... 514/394, 395, 514/449, 365, 372, 388

[56] References Cited

U.S. PATENT DOCUMENTS 5,767,138  6/1998  Camden ................................... 514/365

OTHER PUBLICATIONS

Merck Index, 12th ed., 7943 and 9877, Merck & Co. (NJ 1996).
W. T. Thompson, Agricultural Chemicals, Book IV, Fungicides, pp. 154, 121, 123.
Translation of Delatour et al, Therapie, vol. 31, No.4, pp. 505–515, 1976.
Lacey et al., International Journal for Parasitology, vol. 18 No. 7, pp. 885–936 (1988).

*Primary Examiner*—Jerome D. Goldberg
*Attorney, Agent, or Firm*—R. A. Dabek; J. C. Rasser

[57] ABSTRACT

A pharmaceutical composition that inhibits the growth of tumors and cancers in mammals and can be used to treat viral infections that comprises a fungicide in combination with chemotherapeutic agents is disclosed. The particular fungicide used is a benzimidazole derivative. Potentiators can also be included in the composition.

5 Claims, No Drawings

PHARMACEUTICAL COMPOSITION FOR INHIBITING THE GROWTH OF CANCERS

TECHNICAL FIELD

This invention is a pharmaceutical composition that inhibits the growth of cancers and tumors in mammals, particularly in human and warm blooded animals. It is also effective against viruses and can be used to treat viral infections. The composition contains a benzimidazole derivative.

BACKGROUND OF THE INVENTION

Cancers are the leading cause of death in animals and humans. The exact cause of cancer is not known, but links between certain activities such as smoking or exposure to carcinogens and the incidence of certain types of cancers and tumors has been shown by a number of researchers.

Many types of chemotherapeutic agents have been shown to be effective against cancers and tumor cells, but not all types of cancers and tumors respond to these agents. Unfortunately, many of these agents also destroy normal cells. The exact mechanism for the action of these chemotherapeutic agents are not always known.

Despite advances in the field of cancer treatment the leading therapies to date are surgery, radiation and chemotherapy. Chemotherapeutic approaches are said to fight cancers that are metastasized or ones that are particularly aggressive. Such cytocidal or cytostatic agents work best on cancers with large growth factors, i.e., ones whose cells are rapidly dividing. To date, hormones, in particular estrogen, progesterone and testosterone, and some antibiotics produced by a variety of microbes, alkylating agents, and anti-metabolites form the bulk of therapies available to oncologists. Ideally cytotoxic agents that have specificity for cancer and tumor cells while not affecting normal cells would be extremely desirable. Unfortunately, none have been found and instead agents which target especially rapidly dividing cells (both tumor and normal) have been used.

Clearly, the development of materials that would target tumor cells due to some unique specificity for them would be a breakthrough. Alternatively, materials that were cytotoxic to tumor cells while exerting mild effects on normal cells would be desirable. It is believed that these benzimidazole compositions when used in conjunction with chemotherapeutic agents can reduce the growth of cancers and tumors, including leukemia. It has been found that the benzimidazoles are especially effective in suppressing the growth of the cancer, tumor, virus, or bacteria. The use of these benzimidazoles in combination with other chemotherapeutic agents which are effective in destroying the tumor is a novel method of treatment.

Therefore, it is an object of this invention to provide a pharmaceutical composition that is effective in inhibiting the growth of tumors and cancers in mammals with mild or no effects on normal cells.

More specifically, it is an object of this invention to provide an anti-cancer composition comprising a pharmaceutical carrier and a benzimidazole derivative and a chemotherapeutic agent as defined herein along with a method for treating such cancers.

The benzimidazole compositions are also effective against viruses and can be used to treat viral infections. Therefore it is another object of this invention to provide a method of treating viral infections such as HIV, influenza and rhinoviruses wherein the benzimidazole is administered in conjunction with a potentiator.

These and other objects will become evident from the following detailed description of this inventions.

SUMMARY OF THE INVENTION

A pharmaceutical composition for treatment of mammals, and in particular, warm blooded animals and humans, comprising a pharmaceutical carrier and an effective amount of chemotherapeutic agents and a benzimidazole selected from the group consisting of:

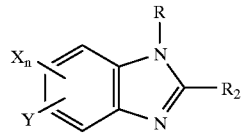

wherein X is hydrogen, halogen, alkyl of less than 7 carbon atoms or alkoxy of less than 7 carbon atoms; n is a positive integer of less than 4; Y is hydrogen, chlorine, nitro, methyl or ethyl; and R is hydrogen, or an alkyl group of from 1 to 8 carbon atoms or $CONHR_3$ and $R_3$ is alkyl of less than 7 carbons, preferably butyl or isobutyl, and $R_2$ is 4-thiazolyl, $NHCOOR_1$ wherein $R_1$ is aliphatic hydrocarbon of less than 7 carbon atoms, and preferably an alkyl group of less than 7 carbon atoms is claimed. Preferably the compositions are:

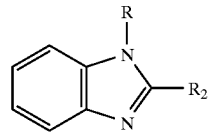

wherein R is hydrogen or $CONHR_3$ and $R_3$ is alkyl of less than 7 carbons, preferably butyl or isobutyl or an alkyl of I through 8 carbon atoms and $R_2$ is selected from the group consisting of 4-thiazolyl, $NHCOOR_1$, wherein $R_1$ is methyl, ethyl or isopropyl and the non-toxic, pharmaceutically acceptable acid addition salts with both organic and inorganic acids. The most preferred compounds are 2-(4-thiazolyl)benzimidazole, methyl -(butylcarbamoyl)-2-benzimidazolecarbamate and 2-methoxycarbonylamino-benzimidazole and those wherein Y is chloro.

These compositions can be used to inhibit the growth of cancers and other tumors in humans or animals by administration of an effective amount either orally, rectally, topically or parenterally, intravenously or by injection into the tumor. Potentiators can also be used with this composition.

DETAILED DESCRIPTION OF THE INVENTION

A. DEFINITIONS:

As used herein, the term "comprising" means various components can be conjointly employed in the pharmaceutical composition of this invention. Accordingly, the terms "consisting essentially of" and "consisting of" are embodied in the term comprising.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will, obviously, vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutical addition salts" is salt of the anti-cancer compound with an organic or inorganic acid. These preferred acid addition salts are chlorides, bromides, sulfates, nitrates, phosphates, sulfonates, formates, tartrates, maleates, malates, citrates, benzoates, salicylates, ascorbates, and the like.

As used herein, a "pharmaceutical carrier" is a pharmaceutically acceptable solvent, suspending agent or vehicle, including liposomes, for delivering the anti-cancer agent to the animal or human. The carrier may be liquid or solid and is selected with the planned manner of administration in mind.

As used herein, "cancer" refers to all types of cancers or neoplasm or malignant tumors found in mammals, including tumors and leukemia.

As used herein, the "anti-cancer compounds" are the benzimidazoles, and their salts. The exact benzimidazoles are described in detail below. The preferred materials are the products sold under the names "thiabendazole®", "benomyl®" and "carbendazim®" by BASF and Hoechst, DuPont and MSD-AgVet.

As used herein "viruses" includes viruses which infect animals or mammals, including humans. Viruses includes HIV, influenza, polio viruses, herpes, rhinoviruses, and the like.

As used herein "chemotherapeutic agents includes DNA-interactive Agents, Antimetabolites, Tubulin-Interactive Agents, Hormonal agents and others, such as Asparaginase or hydroxyurea.

As used herein "potentiators" are materials such as tripro-lidine and its cis-isomer and procodazole which are used in combination with the chemotherapeutic agents and benzimidazoles.

B. THE ANTI-CANCER COMPOUNDS

The anti-cancer compounds are benzimidazole derivatives which are known for their antifungal activities. They are systemic fungicides used to prevent and eradicate fungi. The compounds have the following structure:

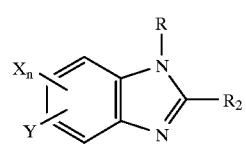

wherein X is hydrogen, halogen, alkyl of less than 7 carbon atoms or alkoxy of less than 7 carbon atoms; n is a positive integer of less than 4; Y is hydrogen, chlorine, nitro, methyl or ethyl; and R is hydrogen, $CONHR_3$ and $R_3$ is alkyl of less than 7 carbons, preferably butyl or isobutyl or an alkyl group having from 1 to 8 carbons, and $R_2$ is 4-thiazolyl, $NHCOOR_1$ wherein $R_1$ is aliphatic hydrocarbon of less than 7 carbon atoms, and preferably and alkyl group of less than 7 carbon atoms. Preferably the compositions are:

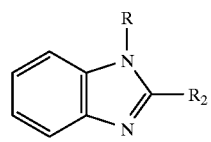

wherein R is hydrogen, $CONHR_3$ and $R_3$ is alkyl of less than 7 carbons, preferably butyl or isobutyl or an alkyl of 1 through 8 carbon atoms and $R_2$ is selected from the group consisting of 4-thiazolyl, $NHCOOR_1$, wherein $R_1$ is methyl, ethyl or isopropyl and the non-toxic, pharmaceutically acceptable acid addition salts with both organic and inorganic acids.

The most preferred compounds are 2-(4-thiazolyl) benzimidazole, methyl-(butylcarbamoyl)-2-benzimidazolecarbamate and 2-methoxycarbonylamino-benzimidazole and the compounds wherein Y is chloro and X is hydrogen.

These compounds are prepared according to the method described in U.S. Pat. No. 3,738,995 issued to Adams et al, Jun. 12, 1973. The thiazolyl derivatives are prepared according to the method described in Brown et al., *J. Am. Chem. Soc.*, 83, 1764 (1961) and Grenda et al., *J. Org. Chem.*, 30, 259 (1965).

It is believed that fungicides, particularly systemic fungicides, have the capability of reducing tumors or decreasing their growth significantly. Systemic fungicides have the ability to migrate through the plant or animal body. While this is a positive attribute, it is not an essential requirement of the effective compounds for treating viral infections, cancers or tumors.

C. CHEMOTHERAPEUTIC AGENTS

The chemotherapeutic agents are generally grouped as DNA-interactive Agents, Antimetabolites, Tubulin-Interactive Agents, Hormonal agents and others such as Asparaginase or hydroxyurea. Each of the groups of chemotherapeutic agents can be further divided by type of activity or compound. The chemotherapeutic agents used in combination with the anti-cancer agents or benzimidazoles of this invention include members of all of these groups. For a detailed discussion of the chemotherapeutic agents and their method of administration, see Dorr, et al, *Cancer Chemotherapy Handbook,* 2d edition, pages 15–34, Appleton & Lange (Connecticut, 1994) herein incorporated by reference.

DNA-Interactive Agents include the alkylating agents, e.g. Cisplatin, Cyclophosphamide, Altretamine; the DNA strand-breakage agents, such as Bleomycin; the intercalating topoisomerase II inhibitors, e.g., Dactinomycin and Doxorubicin); the nonintercalating topoisomerase II inhibitors such as, Etoposide and Teniposide; and the DNA minor groove binder Plcamydin.

The alkylating agents form covalent chemical adducts with cellular DNA, RNA, and protein molecules and with smaller amino acids, glutathione and similar chemicals. Generally, these alkylating agents react with a nucleophilic atom in a cellular constituent, such as an amino, carboxyl, phosphate, sulfhydryl group in nucleic acids, proteins, amino acids, or glutathione. The mechanism and the role of these alkylating agents in cancer therapy is not well understood. Typical alkylating agents include:

Nitrogen mustards, such as Chlorambucil, Cyclophosphamide, Isofamide, Mechlorethamine, Melphalan, Uracil mustard;

aziridines such as Thiotepa;

methanesulfonate esters such as Busulfan;

nitroso ureas, such as Cannustine, Lomustine, Streptozocin;

platinum complexes, such as Cisplatin, Carboplatin;

bioreductive alkylator, such as Mitomycin, and Procarbazine, Dacarbazine and Altretamine;

DNA strand breaking agents include Bleomycin;

DNA topoisomerase II inhibitors include the following:

Intercalators, such as Amsacrine, Dactinomycin, Daunorubicin, Doxorubicin, Idarubicin, and Mitoxantrone;

nonintercalators, such as Etoposide and Teniposide.

The DNA minor groove binder is Plicamycin.

The antimetabolites interfere with the production of nucleic acids by one or the other of two major mechanisms. Some of the drugs inhibit production of the deoxyribonucleoside triphosphates that are the immediate precursors for DNA synthesis, thus inhibiting DNA replication. Some of the compounds are sufficiently like purines or pyrimidines to be able to substitute for them in the anabolic nucleotide pathways. These analogs can then be substituted into the DNA and RNA instead of their normal counterparts. The antimetabolites useful herein include:

folate antagonists such as Methotrexate and trimetrexate pyrimidine antagonists, such as Fluorouracil, Fluorodeoxyuridine, CB3717, Azacytidine, Cytarabine, and Floxuridine purine antagonists include Mercaptopurine, 6-Thioguanine, Fludarabine, Pentostatin;

sugar modified analogs include Cyctrabine, Fludarabine;

ribonucleotide reductase inhibitors include hydroxyurea.

Tubulin Interactive agents act by binding to specific sites on tubulin, a protein that polymerizes to form cellular microtubules. Microtubules are critical cell structure units. When the interactive agents bind on the protein, the cell can not form microtubules Tubulin Interactive agents include Vincristine and Vinblastine, both alkaloids and Paclitaxel.

Hormonal agents are also useful in the treatment of cancers and tumors. They are used in hormonally susceptible tumors and are usually derived from natural sources. These include:

estrogens, conjugated estrogens and Ethinyl Estradiol and Diethylstilbesterol, Chlorotrianisene and Idenestrol;

progestins such as Hydroxyprogesterone caproate, Medroxyprogesterone, and Megestrol;

androgens such as testosterone, testosterone propionate; fluoxymesterone, methyltestosterone;

Adrenal corticosteroids are derived from natural adrenal cortisol or hydrocortisone. They are used because of their anti inflammatory benefits as well as the ability of some to inhibit mitotic divisions and to halt DNA synthesis. These compounds include, Prednisone, Dexamethasone, Methylprednisolone, and Prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include:

antiestrogenic agents such as Tamosifen, antiandrogen agents such as Flutamide ; and antiadrenal agents such as Mitotane and Aminoglutethimide.

Hydroxyurea appears to act primarily through inhibition of the enzyme ribonucleotide reductase.

Asparagenase is an enzyme which converts asparagine to nonfunctional aspartic acid and thus blocks protein synthesis in the tumor.

D. POTENTIATORS

The "potentiators" can be any material which improves or increase the efficacy of the pharmaceutical composition and/or act on the immune system. One such potentiator is triprolidine and its cis-isomer which are used in combination with the chemotherapeutic agents and the benzimidazole. Triprolidine is described in U.S. Pat. No. 5,114,951 (1992). Another potentiator is procodazole, 1H-Benzimidazole-2-propanoic acid; β(2-benzimidazole) propionic acid; 2-(2-carboxyethyl)benzimidazole; propazol) Procodazole is a non-specific active immunoprotective agent against viral and bacterial infections and can be used with the compositions claimed herein. It is effective with the benzimidazoles alone in treating cancers, tumors, leukemia and viral infections or with the combined benzimidazoles and chemotherapeutic agents. Propionic acid and its salts and esters can also be used in combination with the pharmaceutical compositions claimed herein.

The potentiators also improve the efficacy of the benzimidazole compounds in treating viruses and other infections. They can be used in conjunction with these anti-cancer agents in a safe and effective amount. These combinations can be administered to the patient or animal by oral, rectal, topical or parenteral administration.

Antioxidant vitamins such as ascorbic acid, beta-carotene, vitamin A and vitamin E can be administered with the compositions of this invention.

E. DOSAGE

Any suitable dosage may be given in the method of the invention. The type of compounds and the carriers and the amount will vary widely depending on the species of the warm blooded animal or human, body weight, and cancer, or tumor being treated. The range and ratio of the chemotherapeutic agent and anti cancer compound used will depend on the type of chemotherapeutic agent and the cancer being treated. Generally a dosage of between about 2 milligrams (mg) per kilogram (kg) of body weight and about 400 mg per kg of body weight is suitable. Higher dosages, up to 4000 mg/kg can also be used. Preferably from 15 mg to about 1000 mg/kg of body weight is used for the benzimidazoles. For the chemotherapeutic agents, a lower dosage may be appropriate, i.e., from about 0.5 mg/kg of body weight to about 400 mg/kg body weight. Generally, the dosage in man is lower than for small warm blooded mammals such as mice. A dosage unit may comprise a single compound or mixtures thereof with other compounds or other cancer inhibiting compounds. The dosage unit can also comprise diluents, extenders, carriers and the like. The unit may be in solid or gel form such as pills, tablets, capsules, liposomes and the like or in liquid form suitable for oral, rectal, topical, intravenous injection or parenteral administration or injection into or around the tumor.

F. DOSAGE DELIVERY FORMS

The anti-cancer compounds and chemotherapeutic agents are typically mixed with a pharmaceutically acceptable carrier. This carrier can be a solid or liquid or a liposome and the type is generally chosen based on the type of administration being used. The active agent can be coadministered in the form of a tablet or capsule, liposome, or as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from noneffervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms would also include minerals and other materials to make them compatible with the type of injection or delivery system chosen.

Specific examples of pharmaceutical acceptable carriers and excipients that may be used to formulate oral dosage forms of the present invention are described in US. Pat. No. 3,903,297 to Robert, issued Sep. 2, 1975. Techniques and compositions for making dosage forms useful in the present invention are described in the following references: 7 *Modern Pharmaceutics* Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms 2nd Edition* (1976).

G. METHOD OF TREATMENT

The method of treatment can be any suitable method which is effective in the treatment of the particular cancer or tumor type that is being treated. Treatment may be oral, rectal, topical, parenteral or intravenous administration or by injection into the tumor and the like. The method of applying an effective amount also varies depending on the tumor being treated. It is believed that parenteral treatment by intravenous, subcutaneous, or intramuscular application of the benzimodale compounds, formulated with an appropriate carrier, additional cancer inhibiting compound or compounds or diluent to facilitate application will be the preferred method of administering the compounds to warm blooded animals.

These same systemic fungicides can be used alone or in combination with other fungicides along with the chemotherapeutic agents.

Other fungicides that can be used with these materials include 1H-1, 2, 4-triazole derivatives such as fluconazole, and propiconazole, and N-chlorophenythiocarbamates. Herbicides such as N-phosphonoglycine derivatives, e.g. glyphosate can also be used in combination with the benzimidazoles.

The following examples are illustrative and are not meant to be limiting to the invention.

Colon, Breast and Lung Tumor Cells Test

The following cell culture tests were performed to test the toxicity of the benzimidazole compounds on colon, breast and lung human tumor cells. The viability of the cells were tested by looking at MTT (3-[4,5-dimethylthiazol-2-yl]-2, 5-diphenyltetrazolium bromide) reduction. MTT assay is a well known measure of cell viability.

The colon tumor cells (HT29 from American Type Culture Collection (ATCC)) and the breast cells (MX1 from cell lines from ATCC) were cultured in Eagle's Miminal Essential Medium with 10% fetal bovine serum. The lung tumor cells (A549 from ATCC cell lines) were cultured in Ham's F12 medium with 10% fetal bovine serum.

The tumor cells were passaged and seeded into culture flasks at the desired cell densities. The culture medium was decanted and the cell sheets were washed twice with phosphate buffered saline (PBS). The cells were trypsinized and triturated prior to seeding the flasks. Unless otherwise indicated the cultures were incubated at 37±1° C. in a humidified atmosphere of 5±1% carbon dioxide in air. The cultures were incubated until they were 50–80% confluent.

The cells were subcultured when the flasks were subconfluent. The medium was aspirated from the flasks and the cell sheets rinsed twice with PBS. Next, the Trypsin Solution was added to each flask to cover the cell sheet. The Trypsin Solution was removed after 30–60 seconds and the flasks were incubated at room temperature for two to six minutes. When 90% of the cells became dislodged, growth medium was added. The cells were removed by trituration and transferred to a sterile centrifuge tube. The concentration of cells in the suspension was determined, and an appropriate dilution was made to obtain a density of 5000 cells/ml. The cells were subcultured into the designated wells of the 96-well bioassay plates (200 microliter cell suspension per well). PBS was added to all the remaining wells to maintain humidity. The plates were then incubated overnight before test article treatment.

Each dose of test article was tested by treating quadruplicate wells of cultures with 100 microliter of each dilution. Those wells designated as solvent controls received an additional 100 microliter of methanol control; negative controls wells received an additional 100 microliters of treatment medium. PBS was added to the remaining wells not treated with test article or medium. The plates were then incubated for approximately 5 days.

At the end of the 5 day incubation, each dose group was examined microscopically to assess toxicity. A 0.5 mg/ml dilution of MTT was made in treatment medium, and the dilution was filtered through a 0.45 micrometer filter to remove undissolved crystals. The medium was decanted from the wells of the bioassy plates. Immediately thereafter, 2000 microliter of the filtered MTT solution was added to all test wells except for the two untreated blank test wells. The two blank wells received 200 microliters of treatment medium. The plates were returned to the incubator for about 3 hours. After incubation, the MTT containing medium was decanted. Excess medium was added to each well and the plates were shaken at room temperature for about 2 hours.

The absorbance at 550 mn ($OD_{550}$) of each well was measured with a Molecular Devices (Menlo Park, Calif.) VMax plate reader.

The mean $OD_{550}$ of the solvent control wells and that of each test article dilution, and that of each of the blank wells and the positive control were calculated. The mean $OD_{550}$ of the blank wells was subtracted from the mean of the solvent control wells, and test article wells, respectively to give the corresponding mean $OD_{550}$.

$$\% \text{ of Control} = \frac{\text{corrected mean } OD_{550} \text{ of Test Article Dilution}}{\text{corrected mean of } OD_{550} \text{ of Solvent Control}} \times 100$$

Dose response curves were prepared as semi-log plots with % of control on the ordinate (linear) and the test article concentration on the abscissa (logarithmic). The $EC_{50}$ was interpolated from the plots for each test article.

For the test articles administered in methanol, separate responses were prepared to correct for the methanol data.

Adriamycin was used as a positive control. In all cases, it was more toxic than any of the test materials by one or two logs. Adriamycin is one of the more potent agents in current use and one with significant side effects. The peak plasma concentration of other, quite effective chemotherapeutic agents may be 10 to 50 times higher than that of Adriamycin.

The $EC_{50}$ is the concentration at which one half of the cells are killed.

TABLE 1

| | EC-50 Result (ppm) | | | | | |
|---|---|---|---|---|---|---|
| Test Material | HT29 | HT29 | MX1 | MX1 | A549 | A549 |
| Adriamycin | 0.03 | 0.006 | 0.02 | 0.001 | 0.03 | 0.009 |
| benomyl | 0.742 | 0.747 | 1.42 | 2.42 | 0.980 | 1.02 |
| carbendazim | 0.621 | 0.662 | 0.829 | 0.856 | 0.856 | 0.836 |

In normal healthy cells, the following results were obtained. As is evident, the benomyl and carbendazim were much less toxic to normal healthy cells than adriamycin.

TABLE 2

| | EC-50 | | | | | |
|---|---|---|---|---|---|---|
| Test Material | Broncheal Cells | | Kerotinoyle Cells | | Fibroblasts | |
| Benomyl | 0.728 | 0.682 | 3.26 | 2.4 | 3.24 | 2.81 |
| Carbendazin | 0.320 | 0.506 | 0.752 | 0.822 | 1.52 | 1.42 |
| Adriamycin | 0.015 | 0.0020 | 0.0035 | 0.0093 | 0.065 | 0.10 |

In a related study using lung tumor cells (A-549) breast tumor cells (MCF-7) and colon tumor cells (HT-29), thiabendazol, a systemic fungicide, effectively killed these cells. Table 3 summarizes the results

TABLE 3

| | Optical Density | | |
|---|---|---|---|
| Concentration (ppm) | A-549 | MCF-7 | HT-29 |
| 0-Control | 0.600 | 0.245 | 0.398 |
| 173 | 0.007 | 0.007 | 0.005 |
| 35 | 0.411 | 0.025 | 0.011 |
| 17.3 | 0.851 | 0.258 | 0.204 |
| 3.46 | 1.12 | 0.466 | 0.713 |
| 0.87 | 1.32 | 0.507 | 0.852 |

These experiments show that these compositions are effective in killing tumor cells.

EXAMPLE 2

In a mouse model for breast, lung and colon cancer Carbendazim slowed tumor growth. MX1 breast cancer tumors implanted subcutaneously under the mice skin were treated with 500 mg/kg of Carbendazim. Tumor growth was slowed by 42%. Carbendazim slowed tumor growth in lung A549 tumors implanted subcutaneously under the mice skin by 57% at the same dose. In a screening test of HT29 tumors implanted subcutaneously under the mice skin, tumor growth was slowed 54% at 2500 mg/kg dose of Carbendazim.

EXAMPLE 3

In an in vivo mouse model for leukemia, P388, Carbendazin increased the life span of the mice versus control by 129% at 1000 mg/kg; by 148% at 2000 mg/kg and by 189% at 4000 mg/kg.

EXAMPLE 4

In an in vivo mouse model for melanoma, B 16, Carbendazin increased the life span versus control by 131% at 1000 mg/kg; by 163% at 2000 mg/kg and by 187% at 4000 mg/kg.

EXAMPLE 5

When the Carbendazin is combined with Navelbine at 0.5 mg/kg to 2.0 mg/kg, the effective dose of the Carbendazin is lowered in the in vivo mouse model for melanoma.

| Dose Carbendazin (mg/kg) | Dose Navelbine (mg/kg) | % increase in survival time vs. untreated mice |
|---|---|---|
| 4000 | 0.5 | 255 |
| 4000 | 1.0 | 298 |
| 4000 | 2.0 | 268 |
| 2000 | 0.5 | 259 |
| 2000 | 1.0 | 265 |
| 2000 | 2.0 | 287 |
| 1000 | 0.5 | 207 |
| 1000 | 1.0 | 233 |
| 1000 | 2.0 | 245 |
| — | 0.5 | 190 |
| — | 1.0 | 245 |
| — | 2.0 | 265 |

EXAMPLE 6

HIV Chronic Study

Chronic HIV-1 infected cells U1 were derived from an acute HIV-1 infection of the promonocytic cell line, U937. The chronic HIV-1 infected cells, ACH-2 were derived from an acute HIV-1 infection of the T cell line, A3.01.

These cells were cultured in medium and the phorbol ester, PMA. PMA causes the cells (both U1 and ACH-2) to be activated and not divide but it also causes the U-1 cells to differentiate. This results in fewer cells in the PMA-treated cultures than the media alone cultures. Cell viability was measured when these cell lines were treated with the test compounds.

Both cell lines constituitively produce a small amount of HIV-1. ACH-2 cell lines tend to produce more HIV-1 than U1 cells as shown by p-24 ELISA. When either cell line is cultured in the presence of PMA there is an increase in the quantity of HIV-1 produced as measured by the p-24 antigen ELISA.

In addition, the number of institute positive HIV mRNA expressing cells per microscopic field is measured. Comparisons can be made from these numbers since the same number of cells were adhered to the glass slides for each drug concentration ($10 \times 10^6$ cells/ml).

These cells were treated with test samples. Thiabendazole at 60 μg/ml suppressed replication in the HIV monocytes by 74% and the T-cell HIV replication was increased by 26%. The positive control was AZT which suppressed HIV monocytes replication by 98% at 1 μg/ml and suppressed T-cell HIV replication by 60%. The therapeutic index (TI), the ratio of the toxic dose of drug to efficacious dose of drug for thiabendazole is 2.8 versus 12, 500 for AZT.

EXAMPLE 7

In an in vitro acute model for HIV carbendazim inhibited viral replication by 100% at 4 μg/ml and AZT inhibited viral replication by 98% at 1 µg/ml. Thiabendazole inhibited viral replication by 98% at 60 µg/ml.

Benomyl is methyl 1-(butylcarbamoyl)2-benzimidazolecarbamate.

Carbendazin is methyl 2-benzimidazole carbamate.

Thiabendazole is 2-(4-thiazolyl)- 1 H-benzimidazole.

What is claimed is:

1. A method of treating cancer susceptible to treatment in warm blooded mammals comprising administering a safe and effective amount of a pharmaceutical composition comprising a safe and enhanced amount of a benzimodale selected from the group consisting of:

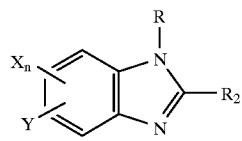

wherein X is hydrogen, halogen, alkyl of less than 7 carbon atoms or alkoxy of less than 7 carbon atoms; n is a positive integer of less than 4; Y is hydrogen, chlorine, nitro, methyl or ethyl; and R is hydrogen, $CONHR_3$ wherein $R_3$ is alkyl of less in 7 carbons or an alkyl group having from 1 to 8 carbon atoms, and $R_2$ is 4thiazolyl or $NHCOOR_1$ wherein $R_1$ is an aliphatic hydrocarbon of less than 7 carbon atoms and the pharmaceutically acceptable organic or inorganic acid addition salts thereof, a safe and effective amount of a chemotherapeutic agent and a safe and effective amount of a potentiator.

2. A method according to claim 1 wherein said chemotherapeutic agent is selected from the group consisting of DNA-interactive Agents, Antimetabolites, Tubulin-Interactive Agents, Hormonal agents, Asparaginase or hydroxyurea.

3. A unit dosage composition for treating cancer susceptible to treatment in animals or humans comprising a safe and enhanced amount of a benzimidazole selected from the group consisting of

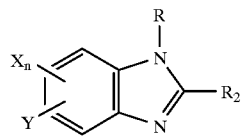

wherein X is hydrogen, halogen, alkyl of less than 7 carbon atoms or alkoxy of less than 7 carbon atoms; n is a positive integer of less than 4; Y is hydrogen, chlorine, nitro, methyl or ethyl; and R is hydrogen, $CONHR_3$ wherein $R_3$ is alkyl of less than 7 carbons or an alkyl group having from 1 to 8 carbon atoms, and $R_2$ is 4-thiazolyl or $NHCOOR_1$ wherein $R_1$ is aliphatic hydrocarbon of less than 7 carbon atoms and pharmaceutically acceptable salts thereof, a safe and effective amount of a chemotherapeutic agent and safe and effective amount of a potentiator.

4. A pharmaceutical composition for treating cancers, tumors or leukemia susceptible to treatment comprising a pharmaceutical carrier and a safe and enhanced amount of a benzimidazole selected from the group consisting of:

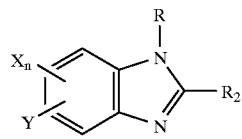

wherein X is hydrogen, halogen, alkyl of less than 7 carbon atoms or alkoxy of less than 7 carbon atoms; n is a positive integer of less than 4; Y is hydrogen, chlorine, nitro, methyl or ethyl; and R is hydrogen $CONHR_3$ wherein $R_3$ is alkyl of less than 7 carbons or an alkyl group having from 1 to 8 carbon atoms, and $R_2$ is 44thiazolyl or $NHCOOR_1$ wherein $R_1$ is aliphatic hydrocarbon of less than 7 carbon atoms, and the pharmaceutically acceptable inorganic or acid addition salts thereof; a safe and effective amount of a chemotherapeutic agent and a safe and effective amount of a potentiator.

5. A pharmaceutical composition for treating cancer susceptible to treatment in animals or humans comprising a safe and enhanced amount of a benzimidazole selected from the group consisting of:

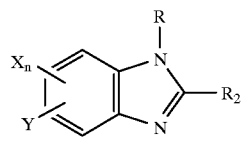

wherein X is hydrogen; Y is hydrogen and R is hydrogen and $R_2$ is $NHCOOR_1$ wherein $R_1$ is an aliphatic hydrocarbon of less than 7 carbon atoms and the pharmaceutically acceptable organic or inorganic acid addition salts thereof; and a safe and effective amount of a chemotherapeutic agent and a safe and effective amount of a potentiator.

* * * * *

UNITED STATES PATENT AND TRADEMARK OFFICE
CERTIFICATE OF CORRECTION

PATENT NO. : 5,929,099  
DATED : July 27, 1999  
INVENTOR(S) : James Berger Camden Page 1 of 2

It is certified that error appears in the above-identified patent and that said Letters Patent is hereby corrected as shown below:

Title Page,  
Insert the following :  
-- Related U.S. Application Data:  
Continuation-in-part of Ser. No. 08/473,817, filed June 7, 1995, abandoned. This application also claims benefit of Provisional appln. Ser No. 60/001,837, filed Aug. 3, 1995. --

Claim 1,  
Line 4 (column 11, line 11), delete "benzimodale" and insert in lieu thereof -- benzimidazole --.  
Line 12 (column 11, line 26), delete "atoms," and insert in lieu thereof -- atoms; --.  
Line 13 (column 11, line 27), delete "4thiazolyl" and insert in lieu thereof-- 4-thiazolyl --.  
Line 14 (column 11, line 28), delete "atoms and" and insert in lieu thereof -- atoms; or --.  
Line 16 (column 11, line 30), delete "thereof," and insert in lieu thereof -- thereof; --.  
Line 17 (column 11, line 31), delete "agent and" and insert in lieu therof -- agent; and --.

Claim 3,  
Line 11 (column 12, line 4), delete "atoms," and insert in lieu thereof -- atoms; --.  
Line 12 (column 12, line 5), delete "atoms and" and insert in lieu thereof -- atoms; or --.  
Line 13 (column 12, line 6), delete "thereof," and insert in lieu thereof -- thereof; --.  
Line 14 (column 12, line 7), delete "agent and" and insert in lieu thereof -- agent; and --.

Claim 4,  
Line 9 (column 12, line 24), delete "hydrogen CONHR$_3$" and insert in lieu thereof -- hydrogen, CONHR$_3$ --.  
Line 11 (column 12, line 26), delete "atoms," and insert in lieu thereof -- atoms; --.  
Line 11 (column 12, line 26), delete "4-4thiazolyl" and insert in lieu thereof -- 4-thiazolyl --.  
Line 12 (column 12, line 27), delete "atoms, and" and insert in lieu thereof -- atoms; or --.

UNITED STATES PATENT AND TRADEMARK OFFICE
CERTIFICATE OF CORRECTION

PATENT NO. : 5,929,099
DATED : July 27, 1999
INVENTOR(S) : James Berger Camden

It is certified that error appears in the above-identified patent and that said Letters Patent is hereby corrected as shown below:

Claim 4,
Line 15 (column 12, line 30), delete "agent and" and insert in lieu thereof -- agent; and --.

Signed and Sealed this

Twenty-seventh Day of November, 2001

*Attest:*

*Attesting Officer*

NICHOLAS P. GODICI
*Acting Director of the United States Patent and Trademark Office*